United States Patent

Laforest et al.

[11] 4,194,003
[45] Mar. 18, 1980

[54] NEW PYRROLE DERIVATIVES, PROCESS FOR THEIR PREPARATION AND THERAPEUTIC APPLICATIONS THEREOF

[75] Inventors: Jacqueline Laforest, Vincennes; Jacqueline Bonnet, Vichy; Pierre Bessin, Chilly-Mazarin, all of France

[73] Assignee: Albert Rolland S.A., Paris, France

[21] Appl. No.: 947,337

[22] Filed: Sep. 26, 1978

[30] Foreign Application Priority Data

Oct. 10, 1977 [GB] United Kingdom ............... 42105/77

[51] Int. Cl.² ...................... A61K 31/40; C07D 207/34
[52] U.S. Cl. .................................. 424/274; 260/326.2; 260/326.25; 260/326.33; 260/326.35; 260/326.36; 260/326.47
[58] Field of Search ...................... 260/326.47, 326.35, 260/326.36, 326.25, 326.33; 424/274

[56] References Cited

U.S. PATENT DOCUMENTS

| | | | |
|---|---|---|---|
| 3,551,571 | 12/1970 | Pachter et al. | 260/326.35 |
| 3,655,693 | 4/1972 | Shen et al. | 260/326.47 |
| 3,721,680 | 3/1973 | Carson | 260/326.47 |
| 4,048,191 | 9/1977 | Carson | 260/326.2 |
| 4,119,639 | 10/1978 | Carson | 260/326.47 |

OTHER PUBLICATIONS

Chem. Abs., vol. 82:p141052y (1976).
Groves et al.; Can. J. Chem., vol. 51, pp. 1089–1098 (1973).
Fischer et al.; Chem. Abs. 29:778⁴ (1935).
Fischer et al.; Chem. Abs. 21:382² (1927).
Nightingale et al.; Chem. Abs., vol. 53:21882f (1959).
Treibs et al.; Chem. Abs., vol. 47:3295h (1952).

Primary Examiner—Mary C. Lee
Attorney, Agent, or Firm—Young & Thompson

[57] ABSTRACT

The present invention relates to a compound selected from the compounds of the formula:

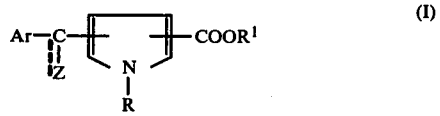

in which:

$R^1$ is selected from hydrogen and $C_{1-4}$ alkyl,

R is selected from $C_{1-6}$ alkyl, benzyl and phenyl,

Ar is selected from phenyl, phenyl monosubstituted with a group selected from $C_{1-4}$ alkyl, $C_{1-4}$ alkoxy and halogen, phenyl polysubstituted with groups selected from $C_{1-4}$ alkyl, $C_{1-4}$ alkoxy and halogen, naphthyl, naphthyl monosubstituted with a group selected from $C_{1-4}$ alkyl, $C_{1-4}$ alkoxy and halogen, naphthyl polysubstituted with groups selected from $C_{1-4}$ alkyl, $C_{1-4}$ alkoxy and halogen, thienyl, furyl and pyrrolyl and > Z represents a carbonyl group, a group of the formula >C=NOH or an alcoholic group >CHOH and the salts of acids of formula (I) with physiologically acceptable bases. Said compounds are useful for the treatment of hyperuricemia.

7 Claims, No Drawings

NEW PYRROLE DERIVATIVES, PROCESS FOR THEIR PREPARATION AND THERAPEUTIC APPLICATIONS THEREOF

The present invention relates to new pyrrole derivatives, to a process for their preparation and to their therapeutic applications, particularly in the treatment of hyperuricemia.

The pyrrole nucleus is the basic structure of porphyrins and some pyrrole derivatives are known as being therapeutically useful, particularly tolmetine (an antiinflammatory drug) having the formula:

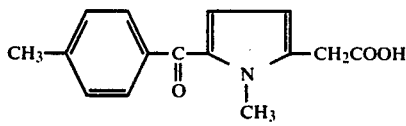

The present invention relates to pyrrole carboxylic acid derivatives having the general formula (I):

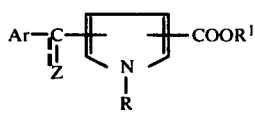

in which:

$R^1$ represents hydrogen or an alkyl group having 1–4 carbon atoms;

R represents an alkyl group having 1–6 carbon atoms, a benzyl group or a phenyl group;

Ar represents an aromatic ring such as a substituted or unsubstituted phenyl group, a substituted or unsubstituted naphthyl group or an aromatic heterocyclic radical such as thienyl, furyl, pyrrolyl and $>C===Z$ represents a carbonyl group ($>C=O$), a group of the formula $>C=NOH$ or an alcoholic group $>CHOH$, and to the salts of the acids of the formula (I) with pharmaceutically acceptable bases.

The phenyl and naphthyl nuclei contemplated here may be mono- or poly-substituted with alkyl, alkoxy, halo groups, the alkyl and alkoxy groups containing 1–4 carbon atoms.

The compounds of the formula (I) in which Z is an oxygen atom may be prepared by acylation of a compound of the formula:

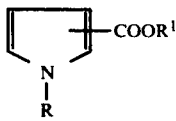

wherein R and $R^1$ have the above-defined meaning, with an acid of the formula ArCOOH or a reactive derivative thereof such as ester, acyl halide or anhydride, Ar having the above-defined meanings. Acylation with an acid is preferably effected in the presence of polyphosphoric acid or an equivalent reagent. Acylation with an acyl halide, anhydride or ester is effected under the known conditions for a Friedel-Crafts reaction. More particularly, acid chloride ArCOCl may be reacted with a compound of the formula (II) dissolved in a solvent such as dichloroethane or methylene chloride, at a temperature below 0° C., and using at least a molar equivalent of a metal chloride, such as AlCl$_3$, SnCl$_4$, as catalyst; said reaction may be followed by hydrolysis of the resulting ester, according to known methods, for example in alcoholic or aqueous-alcoholic medium, in the presence of a base such as a metal hydroxide or carbonate.

Depending on the operating conditions and the reagents used, upon reaction with compound of the formula (II), acylation occurs predominantly at 4- or 5-position of the pyrrole nucleus. Temperatures of less than 0° C. promote acylation at 4-position of the pyrrole-2-carboxylic acid derivatives.

Said isomers may be separated by liquid chromatography or by successive recrystallizations, in view of their solubilities.

The compounds of the formula (I) may also be prepared by substitution of compounds of formula (I) in which R represents H and Ar has the same meaning as above, such substitution being performed by action of an alkyl halide RX in which R is an alkyl radical having 1 to 6 carbon atoms and X is a halogen atom in the presence of an acid-binding agent. The reaction is preferably conducted in a polar aprotic solvent such as dimethyl formamide or dimethylsulfoxide, for example, and in the presence of an alkali hydroxide, and when required, with subsequent hydrolysis of the ester.

The compounds of the formula (I) in which Z is hydroxyimino or represents a secondary alcoholic group may be prepared from ketones of the formula (I) (Z=O) by conventional methods. Thus, the oximes may be obtained by action of hydroxylamine hydrochloride on ketonic acids of the formula (I) or esters thereof, in the presence of a base such as pyridine, which may be used as a solvent, which reaction is followed, whenever required, by hydrolysis of the ester. The alcohols may be prepared by chemical reduction of the ketone functions, for example with sodium borohydride in aqueous-alcoholic solution.

Conversion to salt form of acids of the formula (I) with pharmaceutically acceptable inorganic or organic bases such as metal hydroxides or carbonates or amines, may be effected according to conventional procedures by reacting the acid with the base in a suitable solvent.

The following non limiting Examples illustrate the preparation of compounds of the formula (I). In said examples, the following resulting compounds were submitted to an analytical investigation which confirmed their structure and showed that some of the compounds exhibit various crystalline forms. In the following examples, the melting points mentioned are the instantaneous melting points.

EXAMPLE 1

1-methyl-4-(4-methoxy-1-naphthoyl pyrrole-2-carboxylic acid (a) 4-Methoxy-naphthoic acid chloride (35 g; prepared by action of phosphorous pentachloride on the acid of m.p. 250° C.) followed by methyl 1-methyl-pyrrole-2-carboxylate (22 g) are dissolved in 1,2-dichloroethane (400 ml). To the stirred solution, at about −20° C., is slowly added anhydrous aluminium chloride (23 g). After one hour, the resulting material is poured over 1 kg crushed ice. The organic phase is decanted off and the aqueous phase is extracted with chloroform (500 ml). The organic solution is then dried and the solvents are evaporated off. The solid residue (28 g) is washed with isopropyl ether (200 ml), to give methyl 1-methyl-4-(4-methoxy-1-naphthoyl)-pyrrole-2-carboxylate, m.p. = 162° C., in a yield of 50%.

(b) 24 g of the methyl ester obtained in (a) above are dissolved in 120 ml ethanol and 120 ml aqueous 5 N sodium hydroxide. The solution is heated at the reflux temperature for one hour. After cooling, the material is made acidic with a concentrated aqueous hydrochloric acid solution, and then extracted in methylethylketone, to give 20 g of the desired acid, m.p. = 249° C.

EXAMPLE 2

1-Methyl-4-(3-chloro-benzoyl)-pyrrole-2-carboxylic acid (a) To 100 ml 1,2-dichloroethane are added 5 g 3-chloro-benzoyl chloride followed by 8.4 g aluminium chloride. The mixture is cooled to 5° C. and 4 g methyl 1-methylpyrrole-2-carboxylate dissolved in 15 ml 1,2-dichloroethane are added thereto. The resulting mixture is stirred 0.5 hour at said temperature and then 1 hour at room temperature, after which the solution is hydrolyzed over ice, the organic phase is decanted and the solvent is evaporated off. Recrystallization of the solid residue from methanol give 7.5 g methyl 1-methyl-4-(3-chlorobenzoyl)pyrrole-2-carboxylate, m.p. = 126° C.

As a modification of this reaction 3-chloro benzoic anhydride (10.6 g) is dissolved in nitromethane (120 ml), aluminium chloride (14.5 g) is added and then slowly methyl 1-methyl-pyrrole-2 carboxylate. After 3 hours at room temperature, the mixture is treated in the usual way to gives the ester with 65% yield.

(b) 5 g of the ester obtained in (a) above, dissolved in 60 ml 50% aqueous ethanol, are hydrolyzed by action of 2 g potassium hydroxide. The solution is maintained for 6 hours at the reflux temperature and is then made acidic by addition of hydrochloric acid. The precipitated acid (4.7 g) is recrystallized from 2-butanone or from acetone-water (75:50). M.p. = 214° C.

(c) Action of 1.25 g potassium hydroxide on 5 g of the acid obtained in (b) above dissolved in 50 ml ethanol gives the potassium salt of said acid which melts at 345° C.

(d) As a modification, the acid is prepared in the following manner: 26.7 g aluminium chloride are added to a solution of 17.7 g 3-chlorobenzoic acid chloride in 300 ml 1,2-dichloroethane. At about 0° C., a solution of 12.5 g 1-methylpyrrole-2-carboxylic acid in 200 ml 1,2-dichloroethane is added portionwise. After stirring for 3 hours at room temperature, the mixture is poured over ice. The resulting precipitate is recrystallized from 250 ml 2-butanone, to give 20 g of the pure acid, m.p. = 214° C.

EXAMPLE 3

1-Methyl-4-(α-hydroxy-3-chloro-benzyl)pyrrole-2-carboxylic acid 5 g 1-methyl-4-(3-chloro-benzoyl)pyrrole-2-carboxylic acid (obtained in Example 2) are dissolved in 40 ml aqueous ethanol (96%). 4 ml aqueous sodium hydroxide (d = 1.33) and 0.7 g sodium borohydride are added thereto. After 24 hours at room temperature, the solution is made acidic by addition of acetic acid. 3 g of hydroxylated acid precipitate out; m.p. = 180° C.

EXAMPLE 4

1-Propyl-4-(1-naphthoyl)pyrrole-2-carboxylic acid (a) To a solution of 9 g potassium hydroxide in 25 ml dimethylsulfoxide are added 5 g methyl pyrrole-2 carboxylate and 10 g 1-bromo-propane. After stirring for one hour, the reaction mixture is poured over 100 g crushed ice, after which the solution is extracted with ethyl ether. After drying, the solvent is evaporated under reduced pressure, to give 5 g crude methyl 1-propyl-pyrrole-2-carboxylate.

(b) To 75 ml of a 1,2-dichloroethane solution of 5 g of the ester obtained in (a) above and 5.4 g 1-naphthoyl chloride, at 0° C., are added 3.9 g aluminium chloride. After stirring for ½ hour at 0° C. and then for 1 hour at room temperature, the resulting material is hydrolyzed over ice. The organic phase is decanted and the solvent is evaporated off, to give 5 g of an oil which is then dissolved in 150 ml aqueous ethanol (50%) containing 1 g potassium hydroxide. After refluxing during a few hours, the ethanol is removed under reduced pressure and the aqueous phase is made acidic. The final product is extracted with chloroform. Recrystallization from benzene gives 3.5 g acid which melts at 145° C.; another crystalline form of this acid melts at 175° C.

EXAMPLE 5

1-Methyl-4-(1-naphthoyl)-pyrrole-2-carboxylic acid

Methyl 1-methyl-pyrrole-2-carboxylate (11.2 g) and 1-naphthoyl chloride (15 g) are dissolved in methylene chloride (150 ml) and aluminium chloride (11.3 g) is then slowly added to the resulting solution, with stirring. After 2 hours at the reflux temperature of the solvent, the mixture is poured over 100 g crushed ice and concentrated hydrochloric acid (10 ml) is then added. The decanted organic phase is washed with a basic aqueous solution and is then concentrated, to give 20 g of an oily residue which contains a small amount of starting materials and a mixture of 2-position isomers, i.e., methyl 1-methyl-4- and 5-naphthoyl-pyrrole-2-carboxylates.

The preferentially formed derivative, acylated at 4-position of the pyrrole nucleus, is isolated in view of its lesser solubility in methanol. The 20 g of oil are added to 100 ml refluxing methanol; 11 g methyl 1-methyl-4-naphthoylpyrrole-2-carboxylate precipitate on cooling; m.p. = 124° C.

The material is hydrolyzed by action of a base in aqueous-alcoholic medium, as described in the preceding Examples, to give 9.5 g of the desired acid, m.p. = 216° C.

The morpholine salt of the resulting acid is prepared by action of 1 mole of acid on 1 mole of morpholine, in ethanol solution. It is recrystallized from acetone, m.p. = 155° C.

EXAMPLE 6

1-Methyl-5-(1-naphthoyl)-pyrrole-2-carboxylic acid

The methanol solution obtained in Example 5 after filtration of the methyl 1-methyl-4-(1-naphthoyl)-pyrrole-2-carboxylate is concentrated and the residual oil is submitted to a liquid partition chromatography on a silica column, using 1,2-dichloroethane as eluent. This gives 3 g methyl 1-methyl-5-(1-naphthoyl)-pyrrole-2-carboxylate which melts at 80° C. Hydrolysis of this compound in basic aqueous-alcoholic medium leads to the acid which melts at 174° C.

EXAMPLE 7

1-Methyl-4-(1-naphthoyl-hydroxy-iminomethyl)-pyrrole-2-carboxylic acid 5 g 1-methyl-4-(1-naphthoyl)-pyrrole-2-carboxylic acid obtained in Example 5 and 2 g hydroxylamine hydrochloride are dissolved in 40 ml pyridine and the solution is maintained for 7 hours at a temperature of 60° C. The pyridine is then removed under reduced pressure and the residue is poured over a 2 N aqueous hydrochloric acid solution. The resulting precipitate is isolated, to give, in a yield of 85%, a mixture of the 2 oxime isomers which melt at 252° C., with decomposition.

EXAMPLE 8

Methyl 1-methyl-4-(2-bromo-benzoyl)-pyrrole-2-carboxylate and methyl 1-methyl-5-(2-bromo-benzoyl)-pyrrole-2-carboxylate and corresponding acids Methyl-1-methyl-pyrrole-2-carboxylate (19 g) and 2-bromo-benzoyl chloride (30 g) are dissolved in 1,2-dichloroethane (300 ml) and aluminium chloride (19 g) is slowly added to the resulting solution with stirring. After 3 hours at room temperature the mixture is poured over 500 g of crushed ice. The organic layer is decanted, and after usual treatments concentrated. The solid remaining is crystallized from methyl alcohol; it contains the 2 isomers which are separated by liquid partition chromatography (adsorbent silica, eluent 1,2-dichloroethane),
the product with the benzoyl on C₄ of the pyrrole nucleus melts at 98° C., the other one at 123° C.;
the hydrolysis of these 2 esters by action of potassium hydroxide in refluxing aqueous ethanol gives:

1-methyl-4-(2-bromo-benzoyl)-pyrrole-2-carboxylic acid m.p.=242° C. and 1-methyl-5-(2-bromo-benzoyl)-pyrrole-2-carboxylic acid m.p.=175° C.

EXAMPLE 9

Methyl 1-methyl-4(5)-(3-chloro-benzoyl)-pyrrole-3-carboxylates and acids

A solution of 1-methyl-pyrrole-3-carboxylic acid (6 g) in 1,2-dichloroethane (100 ml) is dropped, at 2° C., on a mixture of 3-chlorobenzoylchloride (8.75 g), aluminium chloride (13.3 g) and 1,2-dichloroethane (100 ml). After 2 hours at 2° C., and 5 hours at room temperature, crushed ice is introduced. The precipitate and organic material dissolved in the organic phase, containing the 2 isomers are esterified to enable separation by liquid chromatography.

8 g of the mixture of acids, so obtained are dissolved in dimethylformamide (150 ml) with methyliodide (8 g) and potassium carbonate (7 g) and maintained at reflux temperature during 5 hours. Water is poured over the mixture and the esters extracted in diethyloxide. The partition chromatography is performed on a silica column, with 1,2-dichloroethane as eluent.

Methyl 1-methyl-4-(3-chloro-benzoyl)-pyrrole-3 carboxylate melts at 86° C. (2.5 g are isolated); 2.5 g of methyl 1-methyl-5-(3-chloro-benzoyl)-pyrrole-3 carboxylate are obtained, melting point: 127° C.

The hydrolysis of these esters with potassium hydroxide in aqueous ethanol gives the acids a yield of 90%.

1-methyl-4-(3-chloro-benzoyl)-pyrrole-3-carboxylic acid melts at 187° C.,
1-methyl-5-(3-chloro-benzoyl)-pyrrole-3-carboxylic acid melts at 218° C.

The compounds of the formula (I) described in the following Examples were prepared according to the previously described procedures.

| Example No | Structural formula | M.P. °C. | Physical constant of the methyl ester. |
|---|---|---|---|
| 10 | naphthyl-C(=O)-pyrrole(N-CH₃)-COOH | 262 | M.p. = 138° C. |
| 11 | naphthyl-C(=O)-pyrrole(N-C₆H₅)-COOH | 214 | |
| 12 | phenyl-C(=O)-pyrrole(N-CH₃)-COOH | 252 | M.p. = 120° C. |

| Example No | Structural formula | M.P. °C. | Physical constant of the methyl ester. |
|---|---|---|---|
| 13 | 4-Cl-C6H4-CO-[1-methylpyrrole-2-COOH] | 216 | M.p. = 160° C. |
| 14 | 2-Cl-C6H4-CO-[1-methylpyrrole-2-COOH] | 238 | M.p. = 102° C. |
| 15 | 3-Cl-C6H4-CO-[1-methylpyrrole-5-COOH] | 200 | |
| 16 | 4-CH3O-C6H4-CO-[1-methylpyrrole-2-COOH] | 204 | M.p. = 135° C. |
| 17 | 3,4,5-(CH3O)3-C6H2-CO-[1-methylpyrrole-2-COOH] | 195 | M.p. = 149° C. |
| 18 | 4-CH3-C6H4-CO-[1-methylpyrrole-2-COOH] | 217 | M.p. = 148° C. |
| 19 | 2,3-(CH3)2-C6H3-CO-[1-methylpyrrole-2-COOH] | 226 | M.p. = 97° C. (oxime of the ester M.p. = 137° C.) |
| 20 | 2,3-Cl2-4-CH3O-C6H2-CO-[1-methylpyrrole-2-COOH] | 275 | M.p. = 190° C. |
| 21 | 3-Cl-C6H4-CO-[1-propylpyrrole-2-COOH] | 191 | |

-continued

| Example No | Structural formula | M.P. °C. | Physical constant of the methyl ester. |
|---|---|---|---|
| 22 | (4-Cl-C6H4)-C(=O)-pyrrole(N-CH2C6H5)-COOH | 140 | |
| 23 | (2,3-diMe-C6H3)-C(=O)-pyrrole(N-CH2C6H5)-COOH | 173 | |
| 24 | (4-Cl-C6H4)-C(=NOH)-pyrrole(N-CH3)-COOH | 230 | |
| 25 | (4-Cl-C6H4)-C(=O)-pyrrole(N-C6H5)-CO2H | 185 | M.p. = 106° C. |
| 26 | (2-furyl)-C(=O)-pyrrole(N-CH3)-CO2H | 214 | M.p. = 132° C. |
| 27 | (2-thienyl)-C(=O)-pyrrole(N-CH3)-CO2H | 210 | M.p. = 145° C. |
| 28 | (N-CH3-pyrrol-2-yl)-C(=O)-pyrrole(N-CH3)-CO2H | 225 | M.p. = 92° C. |

The pharmacological investigation of the compounds of the formula (I) demonstrated that they have an uricosuric activity and are thus applicable in the treatment of pathological hyperuricemias, such as gout, or to prevent an increase of blood uric acid caused by the administration of certain drugs.

This uricosuric activity was evidenced in rats. It appears at as low a dosage as 50 mg/kg with the compounds of this invention and, with some, at a dosage as low as 5 mg/kg, i.e. a dosage which is more than 20 times lower than the $LD_{50}$. The test used is that described in "J. Med. Pharm. Chem. 5 175 (1962)".

This test does not involve a dosage of the uric acid level which is very difficult to perform for rodents, but a study of the elimination rate of a known compound, phenol red, from the blood of rats, following I.V. administration to the animals. It is known that when, prior to phenol red administration, rats are administered known uricosuric compounds such as 2-ethyl-3-benzofuranyl-4-hydroxy-3,5-diido-phenyl ketone, (4-dipropyl-sulfamoyl) benzoic acid or 1,2-diphenyl-(2-phenylsulfinyl)-4-ethylpyrazolidine-3,5-dione, the rate of elimination of the dye from the plasma is reduced.

In such tests, the compounds of this invention have activities comparable to those of the aforementioned compounds, but at dosis that may be reduced by a factor as high as 20.

Thus, the present invention relates also to therapeutic compositions comprising, as active ingredient, a compound of the formula (I), a salt thereof with a pharmaceutically acceptable base or a functional derivative thereof metabolically convertible to said compound, typically in combination with a pharmaceutically acceptable excipient.

The therapeutic compositions of this invention may be administered to humans by the oral or parenteral route.

Said compositions may be formulated typically as capsules, tablets, coated tablets, or injectable suspensions or solutions.

Said compositions may contain typically 1 to 60% by weight of active ingredient, depending on the route of administration.

Doses employed for adult human treatment by oral route are typically in the range of 20–200 mg per day.

Having now described our invention what We claim as new and desire to secure by Letters Patent is:

1. A compound selected from the compounds of the formula

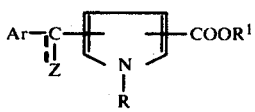
(I)

in which:
R$^1$ is selected from hydrogen and C$_{1-4}$ alkyl,
R is selected from C$_{1-6}$ alkyl, benzyl and phenyl,
Ar is selected from phenyl, phenyl monosubstituted with a group selected from C$_{1-4}$ alkyl, C$_{1-4}$ alkoxy and halogen, phenyl polysubstituted with groups selected from C$_{1-4}$ alkyl, C$_{1-4}$ alkoxy and halogen, naphthyl, naphthyl monosubstituted with a group selected from C$_{1-4}$ alkyl, C$_{1-4}$ alkoxy and halogen, naphthyl polysubstituted with groups selected from C$_{1-4}$ alkyl, C$_{1-4}$ alkoxy and halogen, thienyl, furyl and pyrrolyl
and >C═Z represents a carbonyl group, a group of the formula >C═NOH or an alcoholic group >CHOH
and the salts of acids of formula (I) with physiologically acceptable bases.

2. Compounds as claimed in claim 1, wherein R$^1$ represents a hydrogen atom.

3. Compounds as claimed in claim 1, wherein R represents an alkyl group having 1 to 6 carbon atoms.

4. 1-methyl 4-(3-chlorobenzoyl)pyrrole-2 carboxylic acid, its oxime and their salts with physiologically acceptable bases and their C$_{1-4}$ alkyl esters.

5. 1-methyl 4-(1-naphthoyl)pyrrole-2 carboxylic acid, its oxime and their salts with physiologically acceptable bases and their C$_{1-4}$ alkyl esters.

6. A therapeutic composition having an uricosuric activity containing an uricosuric effective amount of a compound selected from the compounds of the formula

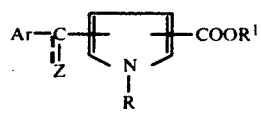
(I)

in which:
R$^1$ is selected from hydrogen and C$_{1-4}$ alkyl,
R is selected from C$_{1-6}$ alkyl, benzyl and phenyl,
Ar is selected from phenyl, phenyl monosubstituted with a group selected from C$_{1-4}$ alkyl, C$_{1-4}$ alkoxy and halogen, phenyl polysubstituted with groups selected from C$_{1-4}$ alkyl, C$_{1-4}$ alkoxy and halogen, naphthyl, naphthyl monosubstituted with a group selected from C$_{1-4}$ alkyl, C$_{1-4}$ alkoxy and halogen, naphthyl polysubstituted with group selected from C$_{1-4}$ alkyl, C$_{1-4}$ alkoxy and halogen, thienyl, furyl and pyrrolyl
and >C═Z represents a carbonyl group, a group of the formula >C═NOH or an alcoholic group >CHOH
and the salts of acids of formula (I) with physiologically acceptable bases
and a pharmaceutically acceptable excipient.

7. A process for the treatment of hyperuricemia which comprises administering to a human in need thereof a therapeutic composition containing an uricosuric effective amount of a compound selected from the compounds of the formula

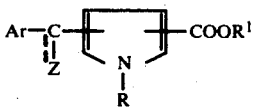
(I)

in which:
R$^1$ is selected from hydrogen and C$_{1-4}$ alkyl,
R is selected from C$_{1-6}$ alkyl, benzyl and phenyl,
Ar is selected from phenyl, phenyl monosubstituted with a group selected from C$_{1-4}$ alkyl, C$_{1-4}$ alkoxy and halogen, phenyl polysubstituted with groups selected from C$_{1-4}$ alkyl, C$_{1-4}$ alkoxy and halogen, naphthyl, naphthyl monosubstituted with a group selected from C$_{1-4}$ alkyl, C$_{1-4}$ alkoxy and halogen, naphthyl polysubstituted with groups selected from C$_{1-4}$ alkyl, C$_{1-4}$ alkoxy and halogen, thienyl, furyl and pyrrolyl
and >C═Z represents a carbonyl group, a group of the formula >C═NOH or an alcoholic group >CHOH
and the salts of acids of formula (I) with physiologically acceptable bases.

* * * * *